(12) United States Patent
Hulliger (10) Patent No.: US 9,603,641 B2
(45) Date of Patent: Mar. 28, 2017

(54) DEVICE FOR OSTEOSYNTHESIS (71) Applicant: DePuy Synthes Products, Inc., Raynham, MA (US)

(72) Inventor: Urs Hulliger, Langendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/807,363

(22) Filed: Jul. 23, 2015

(65) Prior Publication Data
US 2015/0327897 A1  Nov. 19, 2015

Related U.S. Application Data (63) Continuation of application No. 13/150,900, filed on Jun. 1, 2011, now Pat. No. 9,101,423.

(60) Provisional application No. 61/366,324, filed on Jul. 21, 2010.

(51) Int. Cl.
A61B 17/80 (2006.01)

(52) U.S. Cl.
CPC ...... A61B 17/8052 (2013.01); A61B 17/8057 (2013.01)

(58) Field of Classification Search
CPC .................................................. A61B 17/8047
See application file for complete search history.

(56) References Cited

U.S. PATENT DOCUMENTS

| 6,206,882 B1 * | 3/2001 | Cohen ................ A61B 17/7059 |
| | | 606/283 |
| D603,964 S * | 11/2009 | Kriska ......................... D24/155 |
| 7,641,701 B2 | 1/2010 | Kirschman |
| 7,749,257 B2 * | 7/2010 | Medoff ............. A61B 17/8085 |
| | | 606/290 |
| 8,105,367 B2 | 1/2012 | Austin et al. |
| 8,778,000 B2 * | 7/2014 | Haddad ................ A61B 17/809 |
| | | 606/290 |
| 9,295,508 B2 * | 3/2016 | Bottlang .............. A61B 17/808 |
| 2002/0120268 A1 * | 8/2002 | Berger ............... A61B 17/7055 |
| | | 606/300 |
| 2005/0043736 A1 * | 2/2005 | Mathieu ............. A61B 17/8047 |
| | | 606/288 |
| 2006/0200134 A1 | 9/2006 | Freid et al. |

(Continued)

FOREIGN PATENT DOCUMENTS

DE  10 2005 042766  1/2007
FR       2832308     5/2003

(Continued)

Primary Examiner — David Bates
(74) Attorney, Agent, or Firm — Fay Kaplun & Marcin, LLP (57) ABSTRACT A device for osteosynthesis includes a body having a proximal surface, a distal surface configured and dimensioned to face a target portion of bone over which the body is to be mounted and a through opening extending through the body from the proximal surface to the distal surface along a central axis. The through hole includes a first protrusion extending from an inner surface thereof toward the central axis. The first protrusion is biased toward an unstressed state in which the first protrusion extends into the through opening to a first distance from the central axis. The first protrusion is movable toward the inner surface when subjected to a force directed outward from the central axis.

19 Claims, 5 Drawing Sheets (56) References Cited

U.S. PATENT DOCUMENTS

| | | |
|---|---|---|
| 2007/0233116 A1 | 10/2007 | Olerud |
| 2008/0021477 A1 | 1/2008 | Strnad et al. |
| 2008/0147124 A1 | 6/2008 | Haidukewych et al. |
| 2008/0234677 A1 | 9/2008 | Dahners et al. |
| 2008/0234749 A1 | 9/2008 | Forstein |
| 2008/0249573 A1 | 10/2008 | Buhren et al. |
| 2009/0024170 A1 | 1/2009 | Kirschman |
| 2009/0149888 A1 | 6/2009 | Abdelgany |
| 2009/0192549 A1 | 7/2009 | Sanders et al. |
| 2010/0312285 A1 | 12/2010 | White et al. |
| 2011/0015682 A1* | 1/2011 | Lewis ................ A61B 17/8047 606/305 |
| 2011/0118742 A1* | 5/2011 | Hulliger ............. A61B 17/8047 606/70 |
| 2011/0184415 A1* | 7/2011 | Anderson .......... A61B 17/7059 606/70 |
| 2011/0202092 A1* | 8/2011 | Frigg ................ A61B 17/8085 606/289 |
| 2011/0319942 A1* | 12/2011 | Bottlang ............ A61B 17/8004 606/289 |
| 2013/0150900 A1* | 6/2013 | Haddad ................ A61B 17/809 606/290 |
| 2016/0074082 A1* | 3/2016 | Cremer ............. A61B 17/8085 606/70 |

FOREIGN PATENT DOCUMENTS

| | | |
|---|---|---|
| JP | 2006-071014 | 3/2006 |
| WO | 2009/058969 | 5/2009 |
| WO | 2009/148697 | 10/2009 |
| WO | 2012/012029 | 1/2012 |

\* cited by examiner

DEVICE FOR OSTEOSYNTHESIS

PRIORITY CLAIM

The present application is a Continuation Application of U.S. patent application Ser. No. 13/150,900 filed on Jun. 1, 2011, now U.S. Pat. No. 9,101,423; which claims priority to U.S. Provisional Patent Application Ser. No. 61/366,324 filed on Jul. 21, 2010. The entire disclosures of these patents/applications are expressly incorporated herein by reference.

FIELD OF THE INVENTION

The present invention generally relates to a device for osteosynthesis and, in particular, to a bone plate for stabilization of bones.

BACKGROUND OF THE INVENTION

The fixation of osteosynthetic devices to bones is usually effected by means of anchoring elements such as screws and pins. It is sometimes desirable to allow the fixation of the anchoring elements to the osteosynthetic device and the bone at an angle chosen by the surgeon.

A device for osteosynthesis for an angularly stable connection of an anchoring element in a bone plate is known from German Patent No. DE 10 2005 042 766 to Orschler. This known device has the disadvantage that the fixation of an anchoring element and a bone plate is achievable only due to the interaction between a bone screw head with a plate bore. However, as those skilled in the art will understand, increasing forces and loads applied to the bone plate may result in a loosening of the fixation of the bone screw in the plate bore.

SUMMARY OF THE INVENTION

The present invention relates to a device for osteosynthesis allowing an angularly stable connection of an anchoring element (e.g., a bone screw) to an osteosynthetic device (e.g., a bone plate) as well as a rigid locking of the anchoring element in the osteosynthetic device.

In particular, the present invention relates to a device for osteosynthesis comprising a body having a proximal surface, a distal surface configured and dimensioned to face a target portion of bone over which the body is to be mounted and a through opening extending through the body from the proximal surface to the distal surface along a central axis, the through hole including a first protrusion extending from an inner surface thereof toward the central axis, the first protrusion being biased toward an unstressed state in which the first protrusion extends into the through opening to a first distance from the central axis, the first protrusion being movable toward the inner surface when subjected to a force directed outward from the central axis.

The present invention also relates to a device for osteosynthesis, which comprises a proximal surface, a distal surface configured to face a bone in an operative configuration, and a through opening for receiving an anchoring element connecting the proximal and distal surfaces. The through opening has a central axis, an inner surface and a number, N, of protrusions extending therethrough in a direction of the central axis, wherein the protrusions are movable and/or deformable in a direction from the central axis towards the inner surface of the through opening so that the through opening is radially expandable.

In one embodiment of the device, the through opening is radially expandable by at least 2% of the diameter of the through opening.

In a further embodiment of the device, the protrusions comprise front faces facing the central axis wherein the movability/deformability of the protrusions is not based on the deformability of the front faces.

In still a further embodiment of the device, the protrusions and the inner surface of the through opening are formed as a unitary element.

In another embodiment of the device, the protrusions are elastically deformable. This configuration increases the stability of a bone fixation procedure due to a non-positive connection between the osteosynthetic device and a bone fixation element inserted therethrough, as will be described in greater detail later on.

In yet another embodiment of the device, a first one of the protrusions comprises a front face facing the central axis, a circumference of the front face being less than 360°, preferably 190° to 220°. This embodiment is advantageous in that it simplifies a manufacturing process while increasing the holding force of the osteosynthetic device to the bone.

In a further embodiment of the device, the protrusions number between 3 and 6.

In yet a further embodiment of the device, the front faces of the protrusions are circumferentially separated from each other along an inner surface of the through opening.

In still a further embodiment of the device, the through opening has a non-circular cross-section.

In another embodiment of the device, front faces of each of the protrusions have a different surface area f(N).

In another embodiment of the device, front faces of each of the protrusions have an identical surface area f(N).

In yet another embodiment of the device, an inner surface of the through opening without the areas f(N) has a total area F, and wherein the ratio f(N)/F is in the range of 2 to 15%.

In a further embodiment of the device, the ratio f(N)/F is between 20% and 50%.

In again a further embodiment of the device, the surfaces of the front faces of the protrusions comprise a three-dimensional structure, preferably a macro-structure.

In another embodiment of the device, the front faces of the protrusions are provided with a thread or a thread-like structure. In yet another embodiment of the present invention the front faces are provided with lips.

In a further embodiment of the device, the front faces of the protrusions facing the central axis form a virtual body having an essentially circular cross-section when measured orthogonal to the central axis.

In still a further embodiment of the device, the front faces of the protrusions form a virtual body; the virtual body is conical, preferably with a cone angle in the range of 5° to 15° to permit a non-positive connection with a conical screw head.

In another embodiment of the device, the virtual body formed by the front faces of the protrusions facing the central axis has a form of a spherical segment, preferably of a hemisphere. This configuration allows the advantage of a non-positive connection with a spherical screw head.

In again another embodiment of the device, the virtual body formed by the front faces of the protrusions is a cylinder. This configuration allows the advantage of a non-positive connection with a conical screw head.

In still another embodiment of the device, the protrusions are connected to the inner surface by a connecting part; the connecting part is longitudinally aligned with one of the distal surface of the device and the proximal surface of the device. In another embodiment, the connecting part may be positioned to be equidistant from the proximal and distal surfaces.

In yet another embodiment of the device, the front faces are arranged non-parallel to the central axis of the through opening.

In a further embodiment of the device, the front faces are arranged parallel to the central axis of the through opening.

In a further embodiment, back sides of the protrusions are provided with wedge-shaped male elements and the inner surface of the through opening is provided with corresponding cavities. This embodiment allows the advantage that deformation of the protrusions from the central axis towards the inner surface of the through opening causes the male elements to grip the corresponding cavities to increase a stability of a bone fixation procedure.

According to another aspect of the present invention, a bone fixation assembly is provided with at least one anchoring element insertable in the through opening.

BRIEF DESCRIPTION OF THE DRAWINGS

Several embodiments of the present invention will be described in the following by way of example and with reference to the accompanying drawings in which.

DETAILED DESCRIPTION OF THE INVENTION

The present invention relates to a system and method for the fixation of an osteosynthetic device to a bone via a bone fixation device (e.g., a bone screw) in a manner ensuring that there is no loss of bony purchase over time after implantation. An exemplary bone plate according to the present invention comprises a through opening extending therethrough and having a central opening axis. The through opening defines a channel extending therethrough and comprises a first protrusion extending from an inner wall thereof a predetermined distance radially into the channel. The first protrusion is provided with an elastically deformable hinge coupled to the inner surface of the through opening. In another embodiment. the first protrusion is provided with accordioned layers, as will be described in greater detail later on, to aid in radial expansion of the channel. Specifically, the protrusion is configured so that, when subject to a predetermined force (e.g., by a bone fixation screw inserted into the channel), individual layers of the accordioned protrusion radially compress against one another to increase a diameter of the channel and permit the locking insertion of the bone fixation screw into the bone. The exemplary bone plate according to the present invention permits the insertion of a range of bone fixation screws the outer diameters of whose shafts and heads fall within predetermined ranges. It is noted that although embodiments of the invention are described herein with a predetermined number of protrusions, any number of protrusions may be employed without deviating from the spirit and scope of the present invention. Furthermore, although the exemplary system and method is described with respect to osteosynthetic procedures, any other bone fixation procedure may also be performed in the claimed manner without deviating from the spirit and scope of the present invention.

Figure 1:
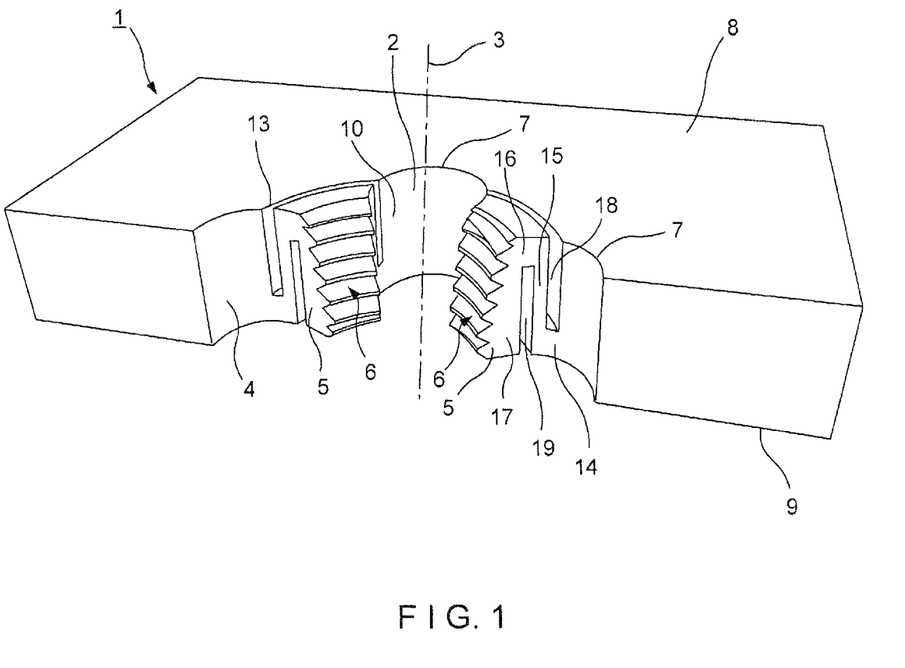
FIG. 1 illustrates a perspective view of a cross-section of an exemplary embodiment of the device according to the present invention.

FIG. 1 illustrates a cross-section of a device 1 according to a first embodiment of the present invention. In an exemplary embodiment, the device 1 is a bone fixation plate having a proximal surface 8, a distal surface 9 configured and dimensioned for facing a bone in an operative configuration and a through opening 2 connecting the proximal surface 8 and the distal surface 9. In an exemplary embodiment, a cross-section of the through opening 2 is substantially clover-shaped and comprises four radial recesses 7 having a first radius of curvature and separated from one another by a plurality of protrusions 5 formed on a portion of the opening having a second radius of curvature, the second radius of curvature being greater than the first radius of curvature, as shown in FIG. 1. That is, the cross-section of the through opening 2 has a form of a tetragon, wherein the angles of the tetragon are extended by the circular radial recesses 7. The through opening 2 has an inner surface 4 and a central axis 3. The protrusions 5 extend from the inner surface 4 of the through opening 2 in the direction of the central axis 3 by a predetermined distance. Specifically, as will be described in greater detail hereinafter, the protrusions 5 are first provided in a biased configuration wherein the protrusions extend into a channel 10 defined by the through opening 2 by a first predetermined distance. Compression of the protrusions 5 causes a reduction of the first predetermined distance to a second smaller distance suitable to permit lockable insertion of a bone fixation device through the channel 10.

Each of the protrusions 5 extends radially into the channel 10 from an inner wall portion 13 having the second radius of curvature as described above. First, second, third and fourth walls 14, 15, 16 and 17 extend out from the inner wall portion 13 in a direction toward the central axis 3. A width of each of the first, second, third and fourth walls 14, 15, 16, 17 is sequentially reduced in a direction approaching the central axis to prevent adjacent ones of the protrusions 5 from contacting one another as they approach a reduced diameter portion of the channel 10 toward the central axis 3, as those skilled in the art will understand. Furthermore, a curvature of each of the first, second, third and fourth walls 14, 15, 16, 17 is substantially similar to a curvature of the inner wall portion 13. Specifically, the first wall 14 extends out from the inner wall 13 at an angle substantially perpendicular to the central axis 3 by a first predetermined distance. In an exemplary embodiment, a distal face of the first wall 14 is aligned with the distal surface 9 of the device 1, the first wall 14 having a longitudinal length smaller than a longitudinal length of the inner wall portion 13. A second wall 15 extends from an end of the first wall 14, the second wall 15 extending substantially parallel to the central axis 3 in a proximal direction, terminating at a proximal end of the inner wall portion 13. A first groove 18 is defined between the second wall 15 and the inner wall portion 13, the first groove 18 allowing for radial compression of the protrusion 5, as will be described in greater detail later on. The third wall 16 extends away from an end of the second wall 15 in a direction also substantially perpendicular to the central axis 3, the third wall 16 being substantially aligned with the proximal surface 8. A length of the third wall is substantially similar to that of the first wall 14. The fourth wall 17 extends distally from an end of the third wall 16, defining a second groove 19 between the fourth wall 17 and the second wall 15. Upon application of a predetermined force from a bone fixation device (not shown), the fourth and second walls 17, 15 are movable/deformable into the first and second grooves 18, 19 so that the through opening 2 is radially expandable. Each of the protrusions 5 shown in FIG. 1 are formed as a single unit Front faces 6 of the fourth walls 17 of the protrusions 5 facing the central axis 3 are provided with a three-dimensional macro-structure in the form of a thread. It is noted, however, that the front faces 6 may be provided with any other surface treatment or shape configured to conform to the outer wall of a head or shaft of a bone fixation device to be inserted therethrough. For example, the surface treatment may be selected to enhance a frictional engagement between the protrusion 5 and the bone fixation element (not shown). Each of the front faces 6 has an area f(N). In the exemplary embodiment shown in FIG. 1, the areas f(N) of each the protrusions 5 are identical to each other. The front faces 6 of the protrusions 5 are arranged at a non-parallel angle relative to the central axis 3 and form a virtual body having a form of a cylindrical cone.

A total area f(T) of all protrusions 5 corresponds to the sum of the areas f(N), i.e.

$$f(T) = f(1) + f(2) + \ldots + f(N-1) + f(N) = \sum_{n=1}^{N} f(n)$$

Figure 5:
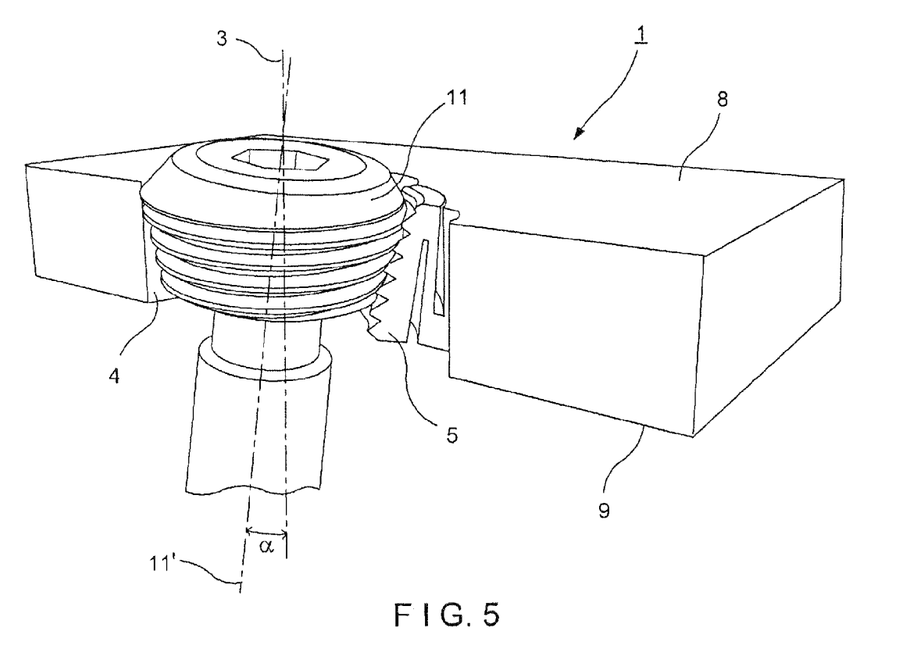
FIG. 5 illustrates a perspective view of a bone fixation assembly comprising the device for osteosynthesis and the anchoring element insertable in the through opening of the device.

In accordance with an exemplary method according to the present invention as shown in FIG. 5, the device 1 may first be positioned over a target portion of a bone being treated. As those skilled in the art will understand, the bone plate may be temporarily held in place (i.e., via a bone pin, etc.). A surgeon or other user may then determine a required angle of insertion of a bone fixation device 1 through the through hole 2. For example, the insertion angle may be selected to permit the bone fixation device to attach bone fragments to one another. The surgeon may then insert the bone fixation device 11 into the through hole at the desired angle so that a longitudinal axis 11' of the bone fixation device 11 is angled relative to the central axis 3 by an angle α. As described in greater detail earlier, the width of the channel 10 may be smaller than a width of a head of the bone fixation device 11 so that, as the head is advanced into the through hole 2, at least a first one of the protrusions 5 is radially compressed. Specifically, as those skilled in the art will understand, the selected angle of insertion will determine which ones of the plurality of protrusions 5 are radially compressed, wherein those protrusions 5 lying in a plane of insertion of the bone fixation device (not shown) may undergo a greater degree of deflection than those separated from the plane of insertion. Each of the protrusions 5 may therefore undergo varying degrees of radial compression, wherein some of the protrusions 5 may not undergo any compression at all. The exemplary protrusions 5 according to the present invention permit a polyaxial insertion of a bone fixation device through the through hole 2 at any desired angle which may be selected prior to or after positioning of the bone plate over the bone.

Figure 2:
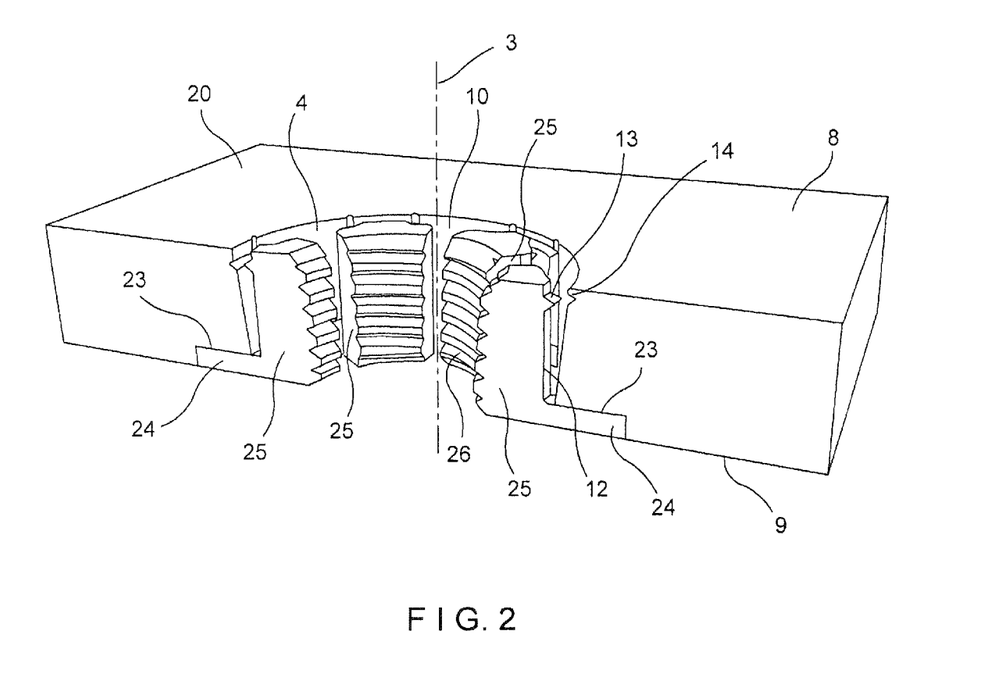
FIG. 2 illustrates a perspective view of another exemplary embodiment of the device according to the present invention.

FIG. 2 illustrates a cross-section of a device 20 according to another embodiment of the present invention, wherein like elements have been referenced with the same reference number. The device 1' comprises the proximal surface 8, distal surface 9 for facing a bone and a through opening 22 connecting the proximal surface 8 and the distal surface 9. The through opening 22 has the inner surface 4 and the central axis 3. The through opening comprises a plurality of protrusions 25 formed substantially similarly as the protrusions 5 of FIG. 1. The protrusions 25 are movable/deformable in the direction from the central axis 3 towards the inner surface 4 of the through opening 22, so that the through opening 22 is radially expandable. A cross-section of the through opening 22 relative to the central axis 3 has a substantially circular shape. Front faces 26 of the protrusions 25 are arranged parallel to the central axis 3 and form a virtual body having the form of a circular cylinder. Areas f(N) of each of the protrusions 25 are substantially identical to each other.

The exemplary protrusions 25 are formed of a separate unit selectively insertable into an opening 23 formed through the inner surface 4 of the through opening 22. As shown in FIG. 2, radially inner walls 12 of the protrusions 5 are provided with wedge-shaped male elements 24 which may be locked in the respectively sized and shaped opening 23. The openings 23 may be longitudinally aligned with the distal surface 9. In one embodiment, the male elements 24 may be bonded to the openings to prevent movement relative thereto. A proximal portion of the inner surface 4 of the through opening 2 may comprise a female opening 14 formed as a pointed groove extending along the inner surface 4 and having a length substantially similar to a length of the radially inner wall 12. The female opening 14 may be sized and shaped to receive an abutment 13 extending along the radially inner wall 12. In an exemplary embodiment, the abutments 13 do not contact the female openings 14 in a first operative configuration. Specifically, the radially inner wall 12 is formed with an angle extending substantially perpendicular to the central axis. In contrast, the inner surface 4 of the through opening 2 is formed with a conical taper so that a diameter of the through opening 2 decreases in a distal direction. Because of this configuration, when the male element 24 is fully seated within the opening 23, a proximal portion of the protrusion including the abutment 13 does not contact the inner surface 4 or female opening 14. Proximal faces 26 of the protrusions 25 are formed with threading or another surface treatment configured to aid in frictional engagement with a bone fixation device and to aid in distal insertion thereof into a bone, as those skilled in the art will understand. As described in greater detail earlier, the front faces 26 may define a virtual conical shape of the channel 10 extending through the through hole 22. It is noted that although the present embodiment is depicted with six protrusions 25, any other number of protrusions may be employed without deviating from the spirit and scope of the present invention. For example, a surgeon may determine a required number of protrusions 25 depending on the requirement for a particular procedure and may add or remove protrusions 25 from the device 20 as needed prior to performing the procedure.

An exemplary method according to the present embodiment is substantially similar to the method discussed above with respect to FIG. 1. After placement of the device 20 over a target portion of the bone, a bone fixation device (not shown) is inserted through the through hole 22 at a selected angle, insertion of the bone fixation device causing at least a portion of the protrusions 25 to deflect radially outward toward the inner surface 4. The protrusions 25 may deflect away from their biased positions by any distance up to a maximum deflection range wherein the abutments 13 come into contact with the female openings 14.

Figure 3:
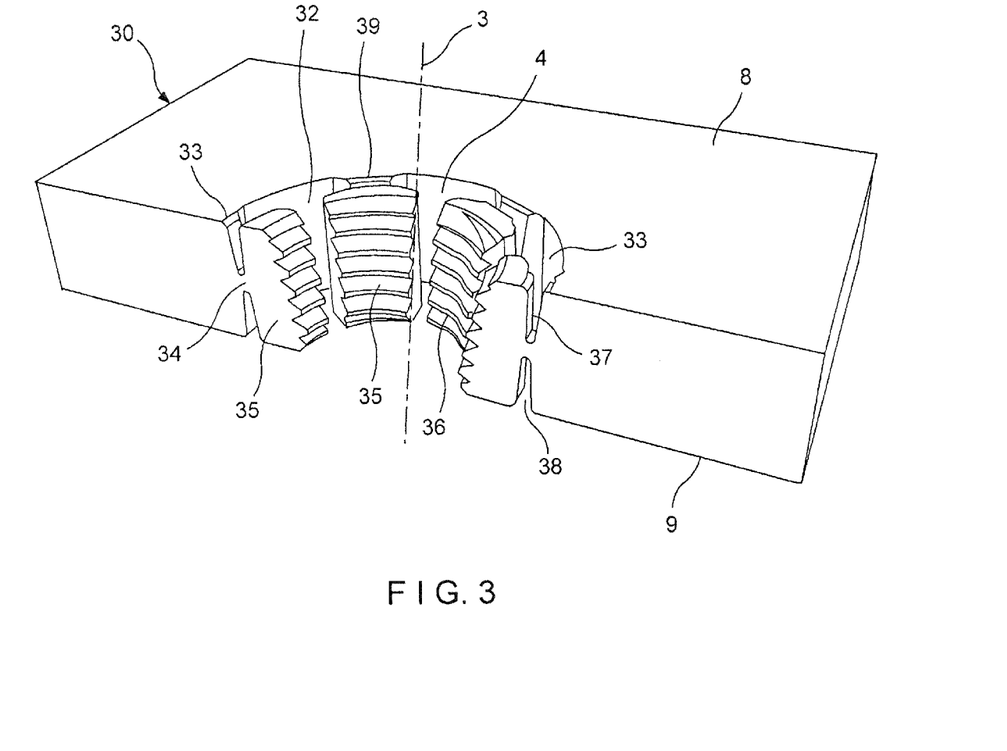
FIG. 3 illustrates a perspective view of a further exemplary embodiment of the device according to the present invention.

FIG. 3 illustrates a cross-section of a device 30 according to another embodiment of the present invention, the device 30 having the proximal surface 8, the distal surface 9 for facing a bone and a through opening 32 connecting the proximal surface 8 and the distal surface 9. The through opening 32 has the inner surface 4 and the central axis 3. The through opening 32 further comprises protrusions 35 extending from the inner surface 4 of the through opening 2. The protrusions 35 are movable/deformable in a direction from the central axis 3 towards the inner surface 4 of the through opening 32 so that the through opening 2 is radially expandable. A cross-sectional shape of the through opening 32 is substantially circular and comprises a plurality of grooves 39 extending along its perimeter, as will be described in greater detail later on. Front faces 36 of the protrusions 35 are arranged non-parallel to the central axis 3 and form a virtual body having a form of a circular cone, as described in greater detail in earlier embodiments.

Each of the protrusions 36 extends radially into the channel 10 from an inner wall 33. The inner wall 33 may be recessed into the inner surface 4 by a predetermined depth so as to create the grooves 39. As those skilled in the art will understand, the recessed inner wall 33 increases the depth by which the protrusions 35 may be deflected from their biased positions upon application of a force by a bone fixation device, thus providing for a greater degree of angulation of the bone fixation device through the through opening 32. A tab 34 extends out of the inner wall 33 at an equidistant position from the proximal and distal surfaces 8, 9. A width of the tab 34 may be substantially equivalent to or smaller than a width of the inner wall 33. The tab 34 and protrusion 35 serve to define proximal and distal grooves 37, 38 therebetween, the grooves 37, 38 permitting deflection of the protrusion 35 thereinto upon application of a predetermined force by a bone fixation device.

Figure 4:
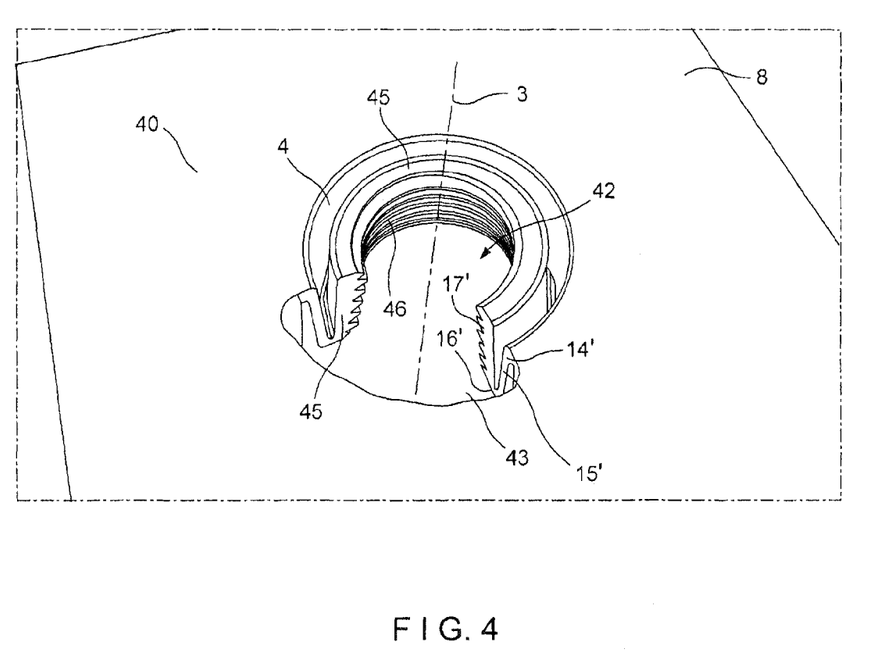
FIG. 4 illustrates a partial perspective view of a further exemplary embodiment of the through opening of a device according to the present invention.

FIG. 4 illustrates a cross-section of a device 40 according to another embodiment of the present invention. The device 40 is formed substantially similarly as the device 1 of FIG. 1 but comprises only a single protrusion 45. The device 40 comprises a through opening 42 having inner surface 4 and central axis 3. A cross-sectional shape of the through opening 42 is substantially circular and is open to a substantially oval opening 43 located adjacent thereto. The protrusion 45 extends through only the substantially circular through opening 42 and is movable/deformable in any direction from the central axis 3 towards the inner surface 4. As described in greater detail with respect to FIG. 1, the protrusion 45 comprises first, second, third and fourth walls 14', 15', 16', 17' permitting radial compression of the through opening 45 upon application of a predetermined minimum force from a bone fixation device. However, whereas the first wall 14 of FIG. 1 was aligned with the distal surface 9, the first wall 14' of the present embodiment is aligned with the proximal surface 8. walls 14, 15, 16, 17 of FIG. 1 Subsequent walls 16', 17' and 18' of the protrusion are then positioned respectively so that a free end of the protrusion is located adjacent the proximal surface 8. However, it is respectfully submitted that the protrusion 45 may also be formed with substantially the same orientation as the protrusions 5 of FIG. 1 without deviating from the spirit and scope of the present invention. A front face 46 of the protrusion 45 is arranged non-parallel to the central axis 3 and forms a virtual body having the form of a circular cone.

The exemplary device 40 of FIG. 4 may be employed in substantially the same manner as discussed with respect to earlier embodiments.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A bone plate, comprising:
    a body having a proximal surface and a distal surface which is configured to face a bone when the body is positioned over a target portion of the bone;
    an opening extending through the body from the proximal surface to the distal surface;
    a first engaging element within the opening and extending along at least a portion of a length of the opening between the proximal and distal surfaces to define a first surface which faces a central axis of the opening and a second surface which faces an inner surface of the opening; and
    a first hinge element connecting the first engaging element to the inner surface, the hinge element extending radially from the inner surface of the body, the hinge defining a proximal groove and a distal groove between the first engaging element and the body so that, when the first engaging element is subjected to a force directed away from the central axis, the first engaging element is deflected toward the inner surface.

2. The bone plate of claim 1, wherein the first surface extends substantially parallel to the central axis.

3. The bone plate of claim 1, wherein the first surface is angled relative to the central axis.

4. The bone plate of claim 1, wherein the first surface includes surface features configured to lockingly engage a head of a bone fixation element.

5. The bone plate of claim 4, wherein the first surface features include a plurality of projections, each of the projections extending at least partly around a circumference of the first surface.

6. The bone plate of claim 1, wherein the first hinge element is received within a correspondingly shaped opening formed along the inner surface.

7. The bone plate of claim 1, wherein the first hinge element and the first engaging element are integrally formed with the inner surface.

8. The bone plate of claim 1, further comprising:
    a second engaging element within the opening and extending along at least a portion of a length of the opening between the proximal and distal surfaces to define a first surface which faces the central axis and a second surface which faces the inner surface, the second engaging element being connected to the inner surface via a second hinge element extending radially from the second surface so that, when the second engaging element is subjected to a force directed away from the central axis, the second engaging element is deflected toward the inner surface, the second engaging element being separated from the first engaging element about a circumference of the opening.

9. The bone plate of claim 8, further comprising:
a third engaging element within the opening and extending along at least a portion of a length of the opening between the proximal and distal surfaces to define a first surface which faces the central axis and a second surface which faces the inner surface, the third engaging element being connected to the inner surface via a third hinge element extending radially from the second surface so that, when the third engaging element is subjected to a force directed away from the central axis, the third engaging element is deflected toward the inner surface, the third engaging element being separated from the first and second engaging elements about a circumference of the opening.

10. The bone plate of claim 9, wherein the first surfaces of the first, second and third engaging elements form portions of a virtual body being one of cylindrical and conical.

11. The bone plate of claim 1, further comprising:
an inner surface groove extending about a portion of a circumference of the inner surface and a correspondingly shaped and sized projection extending radially outward from the second surface of the first engaging element, the inner surface groove being configured to receive the projection when the first engaging element is deflected toward the inner surface.

12. The bone plate of claim 1, wherein the inner surface includes a recess extending therein to increase a distance by which the first engaging element is movable away from the central axis.

13. A device for osteosynthesis, comprising:
a body having a proximal surface and a distal surface which is configured to face a bone when the body is positioned over a target portion of the bone;
an opening extending through the body from the proximal surface to the distal surface;
a plurality of engaging elements within the opening, each of the engaging elements extending along at least a portion of a length of the opening between the proximal and distal surfaces so that each defines a corresponding first surface which faces a central axis of the opening and a second surface which faces an inner surface of the opening; and
a plurality of hinge elements, each of the hinge elements connecting a corresponding one of the engaging elements to the inner surface, each hinge element extending radially from the second surface of a corresponding one of the engaging elements, the hinge elements defining a plurality of proximal grooves and distal grooves between the engaging elements and the body so that, when the engaging elements are subjected to forces directed away from the central axis, the engaging elements are deflected toward the inner surface.

14. The device of claim 13, wherein the first surface of at least one of the engaging elements includes surface features configured to engage a bone fixation element.

15. The device of claim 14, wherein the surface features include a threading.

16. The device of claim 13, wherein each of the engaging elements includes a recess sized and shaped to receive therein at least a part of the corresponding hinge element when the engaging elements are deflected toward the inner surface.

17. The device of claim 13, the hinge element and the engaging elements are integrally formed with the inner surface.

18. The device of claim 13, wherein the first surfaces of the engaging elements combine to form a part of a virtual body being one of cylindrical and conical.

19. The device of claim 13, further comprising:
an inner surface groove extending about a portion of a circumference of the inner surface and a corresponding abutment extending radially outward from the second surfaces of a first one of the engaging elements so that the abutment is received within the inner surface groove when the first engaging element is deflected toward the inner surface.

* * * * *